United States Patent
Thompson

(10) Patent No.: US 9,675,477 B2
(45) Date of Patent: Jun. 13, 2017

(54) WELDED STENT HAVING A WELDED SOLUBLE CORE

(71) Applicant: Medtronic Vascular, Inc., Santa Rosa, CA (US)

(72) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/047,675

(22) Filed: Feb. 19, 2016

(65) Prior Publication Data

US 2016/0167175 A1 Jun. 16, 2016

Related U.S. Application Data

(62) Division of application No. 13/833,588, filed on Mar. 15, 2013, now Pat. No. 9,398,966.

(51) Int. Cl.
*B23K 35/24* (2006.01)
*A61F 2/86* (2013.01)
(Continued)

(52) U.S. Cl.
CPC ............... *A61F 2/86* (2013.01); *A61F 2/95* (2013.01); *A61L 31/022* (2013.01); *A61L 31/148* (2013.01); *B23K 9/007* (2013.01); *B23K 11/11* (2013.01); *B23K 26/22* (2013.01); *B23K 31/02* (2013.01); *A61F 2/966* (2013.01);
(Continued)

(58) Field of Classification Search
CPC ........ A61F 2002/825; A61F 2220/0058; A61F 2240/001; A61F 2250/0031; A61F 2/86; A61F 2/95; A61F 2/966; A61L 31/022; A61L 31/148; B23K 11/11; B23K 26/22; B23K 31/02; B23K 9/007
See application file for complete search history.

(56) References Cited

U.S. PATENT DOCUMENTS 4,739,762 A    4/1988  Palmaz
5,019,090 A *  5/1991  Pinchuk .................... A61F 2/88
                                                          606/1

(Continued)

OTHER PUBLICATIONS

PCT/US2014/026984, PCT International Search Report and Written Opinion, mailed Jul. 14, 2014.

*Primary Examiner* — Erin Saad
*Assistant Examiner* — Carlos Gamino

(57) ABSTRACT

A welded stent and stent delivery system, with a stent including a first strut having a first strut nickel titanium alloy layer and nickel titanium soluble core, the first strut nickel titanium alloy layer being disposed around the first strut nickel titanium soluble core; and a second strut having a second strut nickel titanium alloy layer and nickel titanium soluble core, the second strut nickel titanium alloy layer being disposed around the second strut nickel titanium soluble core, the second strut nickel titanium alloy layer being connected to the first strut nickel titanium alloy layer with a weld. The first and second strut nickel titanium alloy layers are made of a nickel titanium alloy, the first and second strut nickel titanium soluble cores are made of a nickel titanium soluble material, and the weld is made of an alloy of the nickel titanium alloy and the nickel titanium soluble material.

9 Claims, 5 Drawing Sheets

(51) Int. Cl.
- *A61F 2/95* (2013.01)
- *A61L 31/14* (2006.01)
- *A61L 31/02* (2006.01)
- *B23K 9/007* (2006.01)
- *B23K 11/11* (2006.01)
- *B23K 26/22* (2006.01)
- *B23K 31/02* (2006.01)
- *A61F 2/966* (2013.01)
- *A61F 2/82* (2013.01)

(52) U.S. Cl.
CPC . *A61F 2002/825* (2013.01); *A61F 2220/0058* (2013.01); *A61F 2240/001* (2013.01); *A61F 2250/0031* (2013.01)

(56) References Cited

U.S. PATENT DOCUMENTS

| | | |
|---|---|---|
| 5,133,732 A | 7/1992 | Wiktor |
| 5,292,331 A | 3/1994 | Boneau |
| 5,421,955 A | 6/1995 | Lau |
| 6,090,127 A | 7/2000 | Globerman |
| 6,136,023 A * | 10/2000 | Boyle ............... A61F 2/88 623/1.15 |
| 2003/0040772 A1 | 2/2003 | Hyodoh et al. |
| 2005/0131522 A1 | 6/2005 | Stinson et al. |
| 2010/0269950 A1* | 10/2010 | Hoff ............... B21F 45/008 140/123 |
| 2011/0251668 A1 | 10/2011 | Thompson et al. |
| 2012/0067008 A1 | 3/2012 | Bienvenu |

* cited by examiner

WELDED STENT HAVING A WELDED SOLUBLE CORE

RELATED APPLICATIONS

This application is a Division of and claims the benefit of U.S. patent application Ser. No. 13/833,588 filed Mar. 15, 2013. The disclosures of which are herein incorporated by reference in their entirety.

TECHNICAL FIELD

The technical field of this disclosure is medical implant devices, particularly, welded stents and stent delivery systems.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Stents can currently be made of nitinol, which is a nickel titanium alloy. The shape memory and super elastic properties of nitinol are useful in medical devices. Unfortunately, nitinol is difficult to weld because nitinol forms an oxide layer on its surface that makes it difficult for the melt of the weld pool to reach the base metal during the welding process and achieve a good weld. Further, nitinol welds tend to be brittle, increasing the chance of weld failure. Welding difficulties can increase stent manufacturing costs due to increased manufacturing time and added quality control requirements. Poor welds can also decrease the performance of stents in use should the welds fail after implantation in the patient.

Other problems exist with drug eluting stents, which currently employ exterior coatings with or without polymers on metal struts to hold a drug for subsequent elution and delivery of the drug to surrounding tissue. Unfortunately, the coatings can be fragile and can fracture and fragment during manufacture, delivery, deployment, or use. Fracture during manufacture increases the cost and complexity of manufacture. Fracture during delivery, deployment, or use can reduce the effectiveness of the stent due to lost drug and can pose a risk to the patient if fragments block blood flow. The drug elutes from the coating surface, so the duration of drug elution is limited by the coating thickness, i.e., the mean diffusion length of the drug within the polymer coating. Concerns have also been raised over the long-term effects of polymers in contact with the body.

It would be desirable to have a welded stent and stent delivery system that would overcome the above disadvantages.

SUMMARY OF THE INVENTION

One aspect of the invention provides a stent delivery system including a catheter; a sheath disposed around the catheter; and a stent disposed on the catheter. The stent forms a tubular body and includes: a first strut, the first strut having in transverse cross section a first strut nickel titanium alloy layer and a first strut nickel titanium soluble core, the first strut nickel titanium alloy layer being disposed around and immediately adjacent to the first strut nickel titanium soluble core; and a second strut, the second strut having in transverse cross section a second strut nickel titanium alloy layer and a second strut nickel titanium soluble core, the second strut nickel titanium alloy layer being disposed around and immediately adjacent to the second strut nickel titanium soluble core, the second strut nickel titanium alloy layer being connected to the first strut nickel titanium alloy layer with a weld. The first strut nickel titanium alloy layer and the second strut nickel titanium alloy layer are made of a nickel titanium alloy, the first strut nickel titanium soluble core and the second strut nickel titanium soluble core are made of a nickel titanium soluble material, the weld is made of an alloy of the nickel titanium alloy and the nickel titanium soluble material, and the weld further connects the first strut nickel titanium soluble core and the second strut nickel titanium soluble core.

Another aspect of the invention provides a stent forming a tubular body including a first strut, the first strut having in transverse cross section a first strut nickel titanium alloy layer and a first strut nickel titanium soluble core, the first strut nickel titanium alloy layer being disposed around and immediately adjacent to the first strut nickel titanium soluble core; and a second strut, the second strut having in transverse cross section a second strut nickel titanium alloy layer and a second strut nickel titanium soluble core, the second strut nickel titanium alloy layer being disposed around and immediately adjacent to the second strut nickel titanium soluble core, the second strut nickel titanium alloy layer being connected to the first strut nickel titanium alloy layer with a weld. The first strut nickel titanium alloy layer and the second strut nickel titanium alloy layer are made of a nickel titanium alloy, the first strut nickel titanium soluble core and the second strut nickel titanium soluble core are made of a nickel titanium soluble material, the weld is made of an alloy of the nickel titanium alloy and the nickel titanium soluble material, and the weld further connects the first strut nickel titanium soluble core and the second strut nickel titanium soluble core.

Another aspect of the invention provides a method of manufacturing a stent including providing a first strut having in transverse cross section a first strut nickel titanium alloy layer and a first strut nickel titanium soluble core, the first strut nickel titanium alloy layer being disposed around and immediately adjacent to the first strut nickel titanium soluble core, the first strut nickel titanium alloy layer being made of a nickel titanium alloy, the first strut nickel titanium soluble core being made of a nickel titanium soluble material; providing a second strut having in transverse cross section a second strut nickel titanium alloy layer and a second strut nickel titanium soluble core, the second strut nickel titanium alloy layer being disposed around and immediately adjacent to the second strut nickel titanium soluble core, the second strut nickel titanium alloy layer being made of the nickel titanium alloy, the second strut nickel titanium soluble core being made of the nickel titanium soluble material; positioning the first strut adjacent to the second strut at a weld point; at the weld point, melting portions of the first strut nickel titanium alloy layer, the first strut nickel titanium soluble core, the second strut nickel titanium alloy layer, and the second strut nickel titanium soluble core to form a weld pool including the nickel titanium alloy from the first strut nickel titanium alloy layer and the second strut nickel titanium alloy layer, the weld pool further including the nickel titanium soluble material from the first strut nickel titanium soluble core and the second strut nickel titanium soluble core; and cooling the weld pool to form a weld connecting the first strut nickel titanium alloy layer to the second strut nickel titanium alloy layer.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
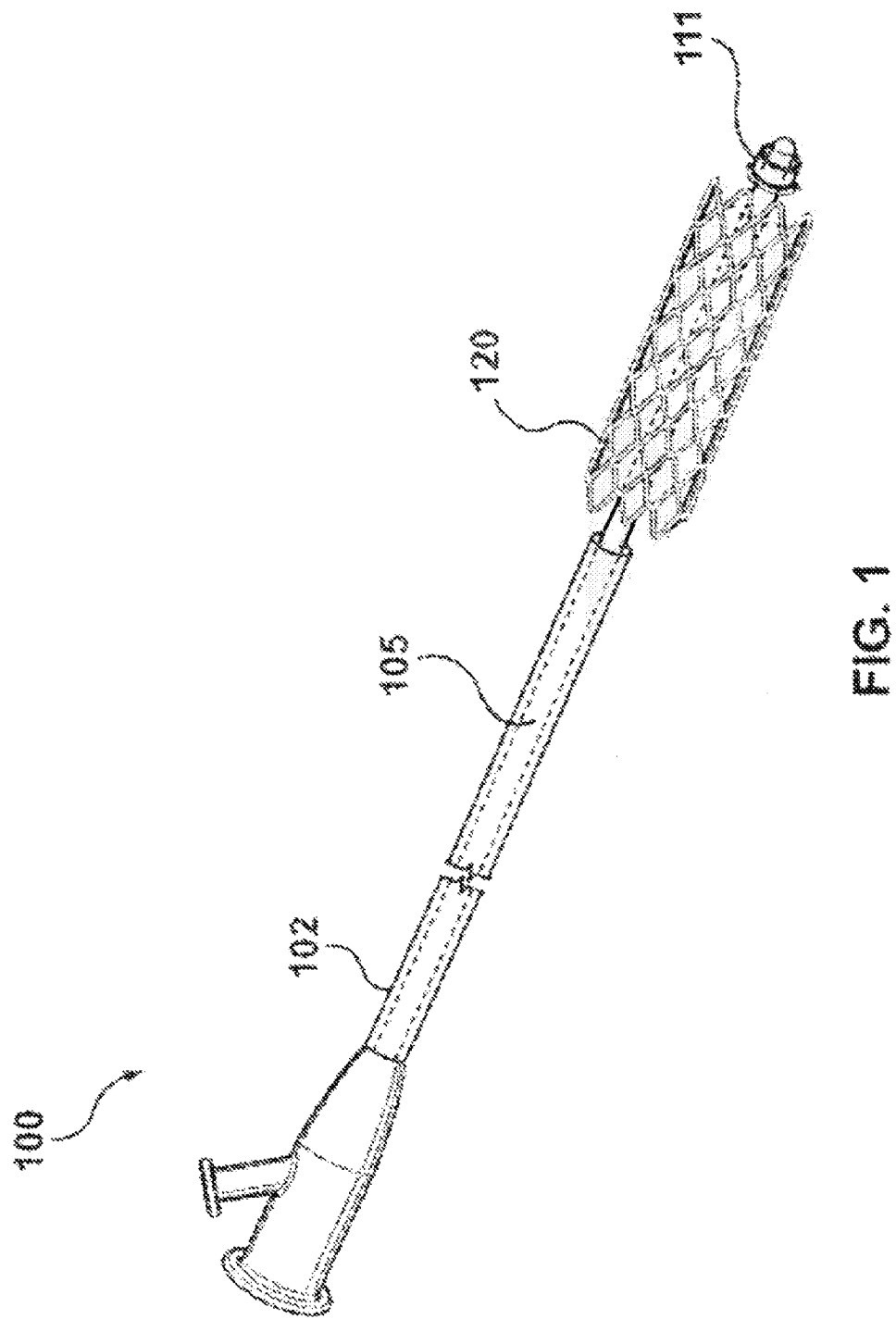
FIG. 1 is a perspective view of a stent delivery system made in accordance with the invention.

FIG. 1 is a perspective view of a stent delivery system made in accordance with the invention. The stent delivery system 100 includes a catheter 105, a sheath 102 disposed around the catheter 105, and a stent 120 disposed on the catheter 105. In this embodiment, the stent 120 is a self-expanding stent. FIG. 1 illustrates the stent delivery system 100 with the stent 120 expanded and deployed after the sheath 102 has been retracted or the catheter 105 has been advanced. Before the stent 120 is deployed, the stent 120 is disposed on the catheter 105 within the sheath 102. The stent 120 is operable for use in a vessel having a vessel wall forming a vessel lumen. The stent 120 is a welded stent in which one or more struts interconnect to form a tubular body. In one embodiment, the stent delivery system 100 can include retention means 111, such as mechanical or adhesive structures, for retaining the stent 120 on the catheter 105 until the stent 120 is deployed.

Figure 2:
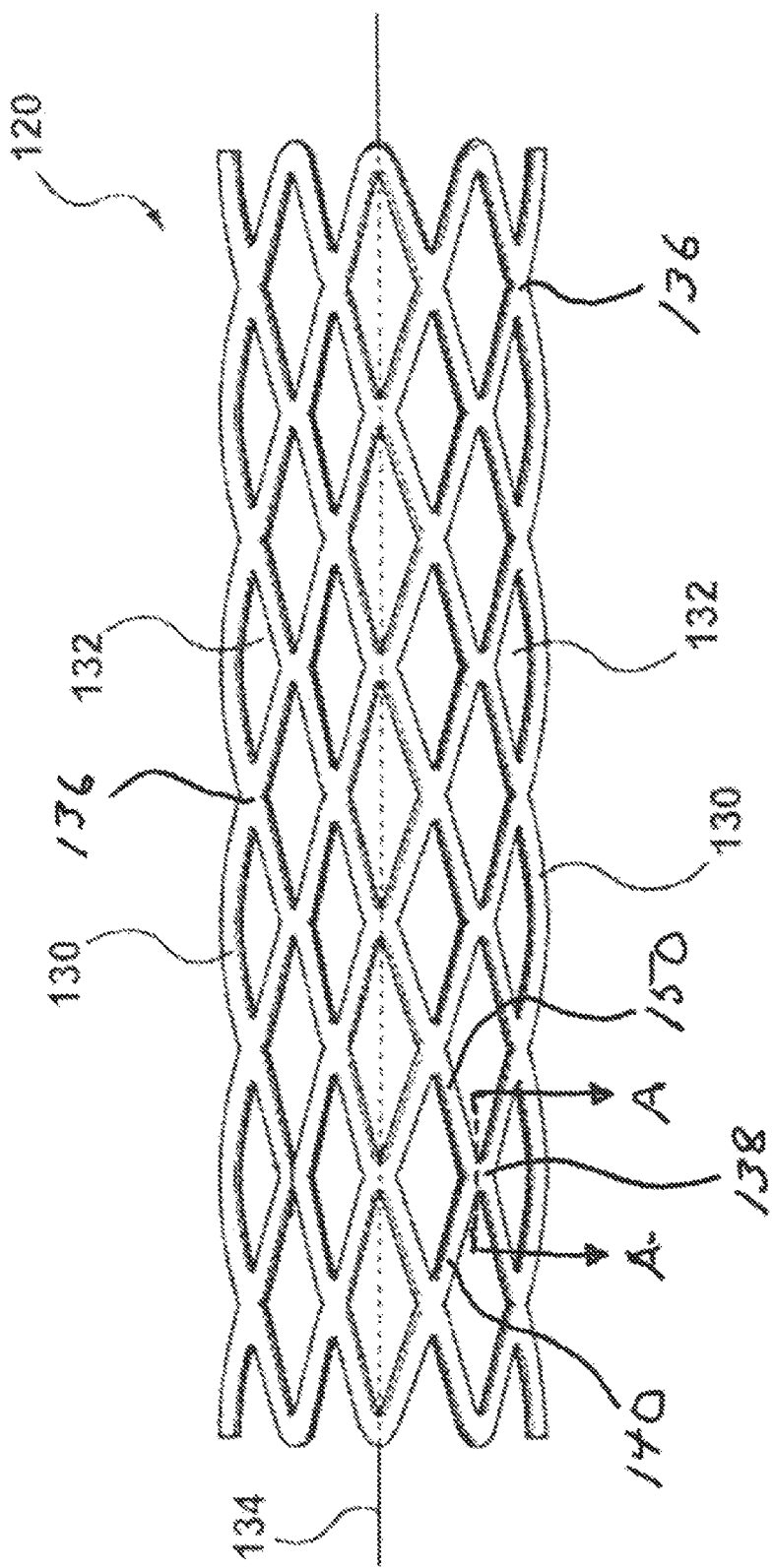
FIG. 2 is a side view of a welded stent made in accordance with the invention.

FIG. 2 is a side view of a welded stent made in accordance with the invention. The stent includes one or more struts interconnected to form a tubular body. The stent can include a first strut having in transverse cross section a first strut nickel titanium alloy layer and a first strut nickel titanium soluble core, with the first strut nickel titanium alloy layer being disposed around and immediately adjacent to the first strut nickel titanium soluble core. The stent can further include a second strut having in transverse cross section a second strut nickel titanium alloy layer and a second strut nickel titanium soluble core, with the second strut nickel titanium alloy layer being disposed around and immediately adjacent to the second strut nickel titanium soluble core. The second strut nickel titanium alloy layer of the second strut can be connected to the first strut nickel titanium alloy layer of the first strut with a weld. The first strut nickel titanium alloy layer and the second strut nickel titanium alloy layer are made of a nickel titanium alloy, and the first strut nickel titanium soluble core and the second strut nickel titanium soluble core are made of a nickel titanium soluble material. The weld is made of an alloy of the nickel titanium alloy (from the first strut nickel titanium alloy layer and the second strut nickel titanium alloy layer) and the nickel titanium soluble material (from the first strut nickel titanium soluble core and the second strut nickel titanium soluble core). In one embodiment, the weld further connects the first strut nickel titanium soluble core and the second strut nickel titanium soluble core. The stent 120 can be installed in the stent delivery system of FIG. 1 for implantation in a body lumen, such as a vessel lumen. In one embodiment, the stent 120 can be self-expanding. In another embodiment, the stent 120 can be expanded by a balloon or another device. When the stent 120 is balloon-expanded, the catheter 105 may be any variety of balloon catheters, such as a PTCA (percutaneous transluminal coronary angioplasty) balloon catheter, capable of supporting a balloon during angioplasty.

Referring to FIG. 2, the stent 120 includes a number of struts 130 interconnected to form the tubular body of the stent 120. The stent 120 includes at least one opening 132 and has a central axis 134 with the openings 132 around the central axis. In one embodiment, the struts 130 can be separate continuous sinusoidal rings encircling the central axis 134, with the peaks of the sinusoidal rings welded together at weld regions 136 where adjacent sinusoidal rings intersect. In another embodiment, the struts 130 can be part of a single sinusoidal wire which spirals around the central axis 134, with the peaks of the single sinusoidal wire welded together at weld regions 136 where adjacent turns of the sinusoidal wire intersect. The pattern of the struts 130 can be W-shaped or can be a more complex shape with the elements of one segment continuing into the adjacent segment.

Those skilled in the art will appreciate that drugs or other therapeutic agents can be applied to the stent 120 for release once the stent is implanted. In one embodiment, an outer drug coating (not shown) can be disposed on at least one of the struts. In one embodiment, the struts can be hollow and filled with one or more drugs or other therapeutic agents, which can be released through perforations (not shown) between the drug-filled central void and the exterior of the struts.

Figure 3:
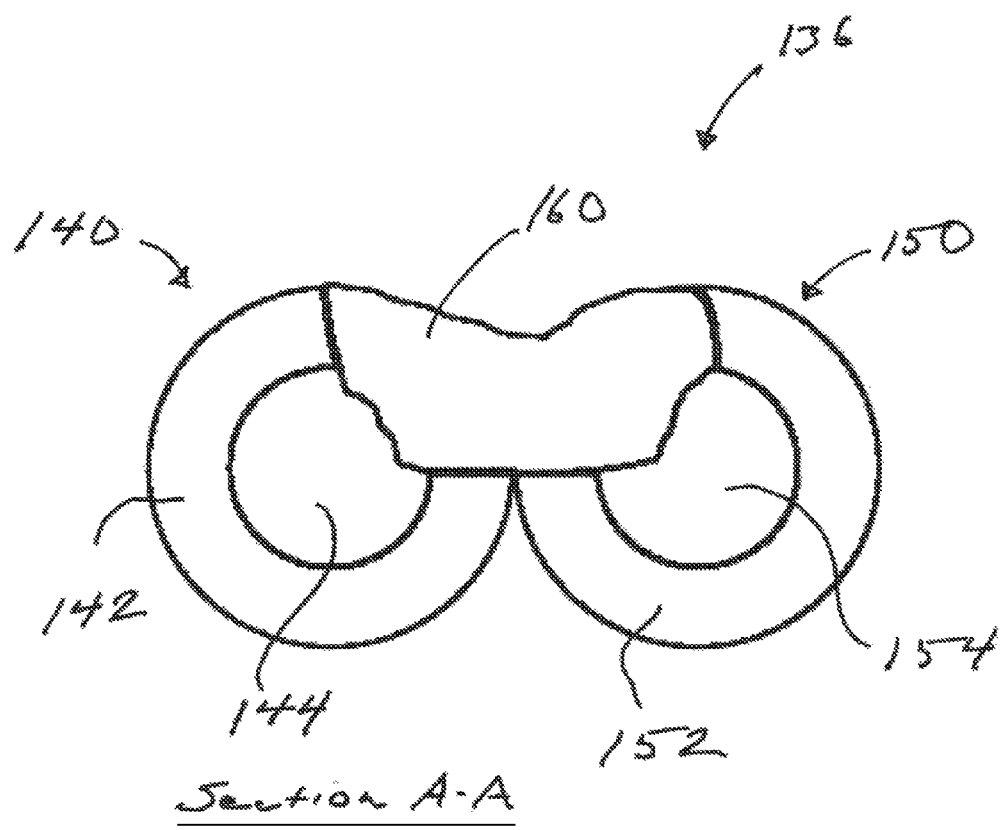
FIG. 3 is a transverse cross section view of a weld region of a welded stent made in accordance with the invention.

The cross section A-A of an exemplary weld region 138 in FIG. 2 with first strut 140 and second strut 150 is illustrated in detail in FIG. 3, which is a transverse cross section view of a weld region of a welded stent made in accordance with the invention.

Referring to FIG. 3, the first strut 140 includes a nickel titanium alloy layer 142 and a nickel titanium soluble core 144. The nickel titanium alloy layer 142 is disposed around and immediately adjacent to the nickel titanium soluble core 144. Similarly, the second strut 150 includes a nickel titanium alloy layer 152 and a nickel titanium soluble core 154. The nickel titanium alloy layer 152 is disposed around and immediately adjacent to the nickel titanium soluble core 154. The nickel titanium alloy layer 142 of the first strut 140 is connected to the nickel titanium alloy layer 152 of the second strut 150 with weld 160. Those skilled in the art will appreciate that the transverse cross section of the struts 140, 150 is not limited to the circular cross section illustrated but can be any cross section (e.g., square, rectangular, ellipsoid, or the like) as desired for a particular application. The dimensions of the nickel titanium alloy layers and the nickel titanium soluble cores can be selected in light of a variety of considerations, such as strut stiffness, weld composition, weldability, and the like. In one example, the strut outer diameter can be in the range of 0.002-0.010 inches. In one example, the thickness of the nickel titanium alloy layer can be in the range of 0.0005-0.004 inches. In one particular example, the strut outer diameter can be 0.007 inches, the diameter of nickel titanium soluble core can be 0.0022 inches, and the thickness of the nickel titanium alloy layer can be 0.0024 inches.

The weld 160 is formed from melting together portions of the nickel titanium alloy layers 142, 152 and the nickel titanium soluble cores 144, 154. The nickel titanium alloy layers 142, 152 are made of a nickel titanium alloy, commonly known as nitinol. The nickel titanium soluble cores 144, 154 are made of one or more nickel titanium soluble materials, which are defined herein as materials such as metals, mixtures, or alloys which are soluble with a nickel titanium alloy melt during welding. Exemplary nickel titanium soluble materials include chromium, molybdenum, iron, and cobalt, singly or in combination as mixtures or alloys.

The nickel titanium soluble materials for the nickel titanium soluble cores 144, 154 are selected to form a weld 160 having the desired strength and flexibility for a particular application. In one embodiment, the nickel titanium soluble material is molybdenum, which produces a weld of a nickel titanium molybdenum alloy. Exemplary nickel titanium molybdenum alloys can include nickel in the range of 45 to 55 percent, titanium in the range of 40 to 45 percent and molybdenum in the range of 5 to 10 percent. The molybdenum in the nickel titanium soluble core can be maintained in place or can be removed to generate a central void within the nickel titanium alloy layer. Optionally, the central void can be filled with a drug or other therapeutic agent to be released after deployment through perforations in the nickel titanium alloy layer between the drug-filled central void and the exterior of the struts. In another embodiment, the nickel titanium soluble material is a chromium molybdenum alloy, which produces a weld of a nickel titanium chromium molybdenum alloy, utilizing the same constituents as a commercially known alloy by the name of Hastelloy C4. Exemplary nickel titanium chromium molybdenum alloys can include nickel in the range of 60 to 70 percent, titanium in the range of 0.5 to 1.0 percent, chromium in the range of 14 to 18 percent and molybdenum in the range of 14 to 17 percent. Other exemplary nickel titanium soluble materials include chromium and iron, utilizing the same constituents as a commercially known alloy by the name of Nimonic 75 (Ni 20-Cr 5-Fe0.6Ti), as well as chromium and cobalt, utilizing the same constituents as a commercially known alloy by the name of Nimonic 90 (Ni 20-Cr 18-Co 3-Ti). Those skilled in the art will appreciate that the nickel titanium soluble material for the nickel titanium soluble core can be selected as desired for a particular application. Those skilled in the art will further appreciate that many of the benefits of commercial alloys, such as Hastelloy C4, Nimonic 75, or Nimonic 90, can be achieved without requiring the exact constituent percentages of the commercial alloy.

Figure 4A:
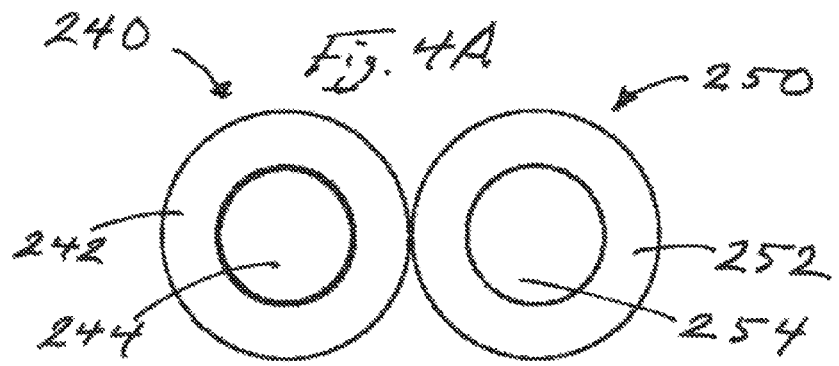
FIGS. 4A-4C are transverse cross section views of a weld region in a method of manufacture of a welded stent in accordance with the invention.
Figure 4B:
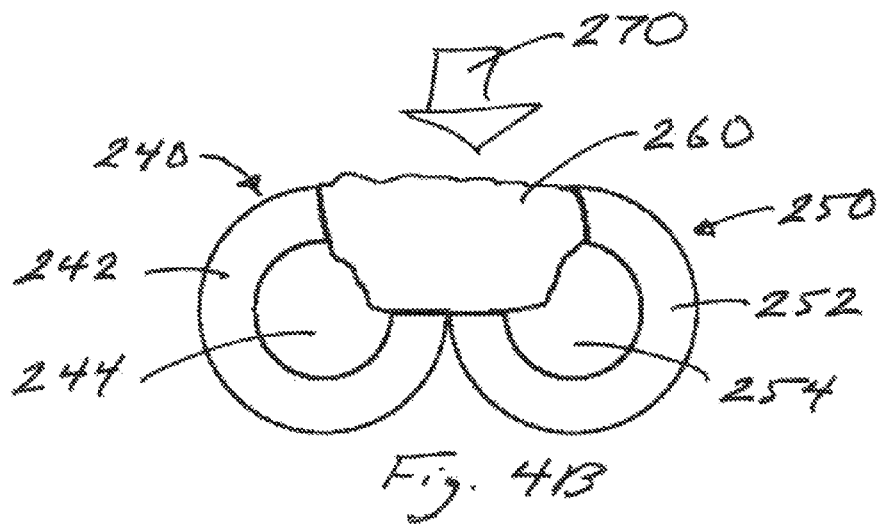
Figure 4C:
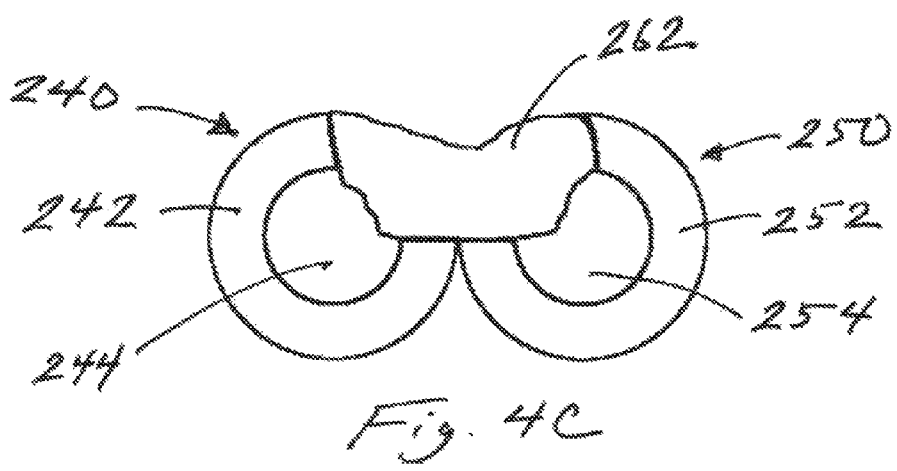

FIGS. 4A-4C, in which like elements share like reference numbers, are transverse cross section views of a weld region in a method of manufacture of a welded stent in accordance with the invention.

FIG. 4A is a transverse cross section view of a weld region in a method of manufacture of a welded stent before welding. The first strut 240 includes a first strut nickel titanium alloy layer 242 and a first strut nickel titanium soluble core 244. The second strut 250 includes a second strut nickel titanium alloy layer 252 and a second strut nickel titanium soluble core 254. The first strut 240 is positioned adjacent the second strut 250 at the weld point.

FIG. 4B is a transverse cross section view of a weld region in a method of manufacture of a welded stent during welding. Energy 270 is applied to the first strut 240 and the second strut 250 to melt portions of the nickel titanium alloy layers 242, 252 and the nickel titanium soluble cores 244, 254, to form a weld pool 260. The weld pool 260 is a mixture of nickel titanium alloy and nickel titanium soluble material in predetermined percentages to produce the alloy desired for the weld. The nickel titanium alloy layers 242, 252 are made of a nickel titanium alloy, commonly known as nitinol. In one embodiment, the nickel titanium soluble cores 244, 254 are made of molybdenum, so that the weld pool 260 is a mixture of nickel, titanium, and molybdenum. In another embodiment, the nickel titanium soluble cores 244, 254 are made of a molybdenum chromium alloy, so that the weld pool 260 is a mixture of nickel, titanium, molybdenum, and chromium. Other exemplary nickel titanium soluble materials include chromium, molybdenum, iron, and cobalt, singly or in combination as mixtures or alloys. The welding parameters and the size of the weld pool can be controlled to form a weld pool that will produce the desired weld for a particular application. Exemplary welding methods include arc welding, laser welding, and resistance welding.

FIG. 4C is a transverse cross section view of a weld region in a method of manufacture of a welded stent after welding. The weld 262 forms from cooling of the weld pool 260. The weld 262 connects the nickel titanium alloy layers 242, 252 and can also connect the nickel titanium soluble cores 244, 254. In one embodiment, the nickel titanium soluble cores 244, 254 can be removed to form central voids, which can be left hollow or filled with a drug or other therapeutic agent.

Figure 5:
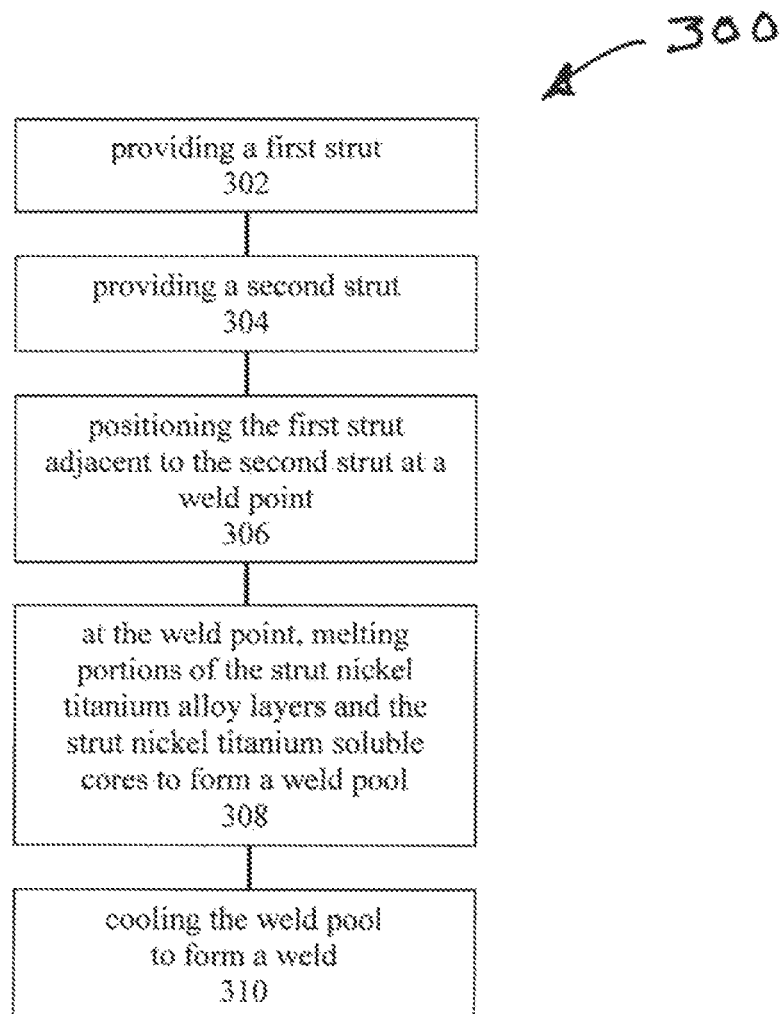
FIG. 5 is a flow chart of a method of manufacture of a welded stent in accordance with the invention.

FIG. 5 is a flow chart of a method of manufacture of a welded stent in accordance with the invention. The method of manufacturing a stent 300 includes providing a first strut 302 having in transverse cross section a first strut nickel titanium alloy layer and a first strut nickel titanium soluble core, the first strut nickel titanium alloy layer being disposed around and immediately adjacent to the first strut nickel titanium soluble core, the first strut nickel titanium alloy layer being made of a nickel titanium alloy, the first strut nickel titanium soluble core being made of a nickel titanium soluble material; providing a second strut 304 having in transverse cross section a second strut nickel titanium alloy layer and a second strut nickel titanium soluble core, the second strut nickel titanium alloy layer being disposed around and immediately adjacent to the second strut nickel titanium soluble core, the second strut nickel titanium alloy layer being made of the nickel titanium alloy, the second strut nickel titanium soluble core being made of the nickel titanium soluble material; positioning the first strut adjacent to the second strut at a weld point 306; at the weld point, melting portions of the first strut nickel titanium alloy layer, the first strut nickel titanium soluble core, the second strut nickel titanium alloy layer, and the second strut nickel titanium soluble core to form a weld pool 308 including the nickel titanium alloy from the first strut nickel titanium alloy layer and the second strut nickel titanium alloy layer, the weld pool further including the nickel titanium soluble material from the first strut nickel titanium soluble core and the second strut nickel titanium soluble core; and cooling the weld pool to form a weld 310 connecting the first strut nickel titanium alloy layer to the second strut nickel titanium alloy layer.

The providing a first strut 302 and the providing a second strut 304 includes providing struts with nickel titanium alloy layers disposed around nickel titanium soluble cores. In one embodiment, the first strut and second strut are part of separate continuous sinusoidal rings. In another embodiment, the first strut and second strut are part of a single sinusoidal wire.

The nickel titanium alloy layers and nickel titanium soluble cores of the struts provide the source material for welding the first strut to the second strut. The composition of the nickel titanium alloy layers and nickel titanium soluble cores can be selected to form a weld having the desired strength and flexibility for a particular application. The nickel titanium alloy layers are made of a nickel titanium alloy, commonly known as nitinol. Exemplary nickel titanium soluble cores can be made of molybdenum or a molybdenum-chromium alloy. Other exemplary nickel titanium soluble materials include chromium, iron, and cobalt, sinqularly or in combination as mixtures or alloys. Particular exemplary combinations of nickel titanium soluble materials include chromium and iron, which produces a nickel titanium chromium iron weld, as well as chromium and cobalt, which produces a nickel titanium chromium cobalt weld. In one embodiment, the struts can include perforations through the walls of the struts between the central void and the exterior of the struts to permit removal of the nickel titanium soluble core from the central void within the nickel titanium alloy layer and optionally to permit filling of the central void with a drug or therapeutic agent.

The positioning the first strut adjacent to the second strut at a weld point 306 can include positioning the struts with the assistance of a jig or other device to assist welding. Once welded, the struts of the stent form a tubular body. The first strut and the second strut can optionally be prepared for welding by cleaning, degreasing, or the like.

The melting portions of the strut nickel titanium alloy layers and the strut nickel titanium soluble cores to form a weld pool 308 can include selecting welding parameters, such as duration, temperature, energy deposition, and the like, to form a suitable weld pool for the particular application, depending on the materials of the strut nickel titanium alloy layers and the strut nickel titanium soluble cores. The size of the weld pool can be controlled to melt a desired amount of material from the strut nickel titanium alloy layers and the strut nickel titanium soluble cores to form a weld pool and subsequent weld of the desired composition. Suitable welding methods include arc welding, laser welding, and resistance welding.

The cooling of the weld pool to form a weld 310 can include controlling cooling rate and annealing the weld to form the desired phase and crystalline structure in the weld.

In one embodiment, the nickel titanium soluble core of the first strut is connected to the nickel titanium soluble core of the second strut by the weld.

The method of manufacturing a stent 300 can further include removing the first strut nickel titanium soluble core to form a first strut central void, which can be left hollow as a central void or filled with a drug or other therapeutic agent. The nickel titanium soluble cores can be removed in one or more of the struts, or all of the struts. When the nickel titanium soluble material is molybdenum, xenon difluoride can be used to vaporize and remove the molybdenum. In one example, a core of molybdenum reacts with xenon difluoride ($XeF_2$) gas at low pressure (1-6 Torr) and relatively high temperature (approximately 150° C.) to form molybdenum hexafluoride ($MoF_6$) and xenon (Xe) gases, which can be exhausted to form a central void within the strut nickel titanium alloy layer. In one embodiment, the xenon difluoride is introduced to the molybdenum through perforations in the wall of the strut nickel titanium alloy layer, and the resulting molybdenum hexafluoride and xenon gases exhaust through the perforations to the exterior of the struts. In another embodiment, the xenon difluoride is introduced to the molybdenum of the nickel titanium soluble core which is exposed at open ends of the struts, and the resulting molybdenum hexafluoride and xenon gases exhaust through the open ends. The open ends can then be sealed if desired.

After forming a strut central void, the method of manufacturing a stent 300 can further include filling the first strut central void with a drug or therapeutic agent. One or more of the strut central voids, or all the strut central voids, can be filled. In one example, a drug or therapeutic agent solution is drawn into the strut central void by capillary action, then the drug or therapeutic agent solution can be solidified. In one embodiment, the drug or therapeutic agent is introduced to the central void through perforations in the wall of the strut nickel titanium alloy layer, through which the drug or therapeutic agent is released after the stent is implanted in a patient. In another embodiment, the drug or therapeutic agent is introduced to the central void through an open end of the struts, which can then be sealed if desired. Perforations can then be formed in the strut nickel titanium alloy layer between the drug-filled central void and the exterior of the struts to allow release of the drug or therapeutic agent after implantation.

Drug, as defined herein, includes any drug, therapeutic agent, bioactive agent, or the like intended to affect the structure or any function of the body of man or other animals. The drug can include a polymer and a drug, or a drug alone. Exemplary drugs include any drug, therapeutic agent, or bioactive agent that can diffuse through a selected polymer, such as an antirestenotic drug (e.g., rapamycin, rapamycin analogue, or rapamycin derivative to prevent or reduce the recurrence or narrowing and blockage of the bodily vessel), an anti-cancer drug (e.g., camptothecin or other topoisomerase inhibitors), an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, a combination thereof, and the like.

A drug coating can be applied to the exterior of the stent if desired. The drug coating can include a polymer and a drug, or a drug alone. Exemplary polymers include any polymer compatible with a selected drug or therapeutic agent, i.e., polymers such as BioLinx® polymer, poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, combinations thereof, and the like.

It is important to note that FIGS. 1-5 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A method of manufacturing a stent comprising:
providing a first strut having in transverse cross section a first strut nickel titanium alloy layer and a first strut soluble core, the first strut nickel titanium alloy layer being disposed around and immediately adjacent to the first strut soluble core, the first strut nickel titanium alloy layer being made of a nickel titanium alloy, the first strut soluble core being made of a soluble material;
providing a second strut having in transverse cross section a second strut nickel titanium alloy layer and a second strut soluble core, the second strut nickel titanium alloy layer being disposed around and immediately adjacent to the second strut soluble core, the second strut nickel titanium alloy layer being made of the nickel titanium alloy, the second strut soluble core being made of the soluble material;
positioning the first strut adjacent to the second strut at a weld point;
at the weld point, melting portions of the first strut nickel titanium alloy layer, the first strut soluble core, the second strut nickel titanium alloy layer, and the second strut soluble core;
at the weld point, mixing the melted portions of the first strut nickel titanium alloy layer, the second strut nickel titanium alloy layer, the first soluble core, and the second soluble core to form a weld pool; and
cooling the weld pool to form a weld connecting together the first strut nickel titanium alloy layer, the second strut nickel titanium alloy layer, the first soluble core, and the second soluble core;
wherein the soluble material is selected from the group consisting of chromium, molybdenum, mixtures thereof, and alloys thereof.

2. The method of claim 1 wherein the weld further connects the first strut soluble core and the second strut soluble core.

3. The method of claim 1 further comprising removing the first strut soluble core to form a first strut central void.

4. The method of claim 3 further comprising filling the first strut central void with a drug.

5. The method of claim 3 wherein the first strut nickel titanium alloy layer includes perforations between the first strut soluble core and the exterior of the first strut, and the removing comprises removing the first strut soluble core through the perforations.

6. The method of claim 1 wherein the soluble material is molybdenum, the method further comprising contacting the first strut soluble core with xenon difluoride to form a first strut central void.

7. The method of claim 1 wherein the soluble material is molybdenum and the weld is a nickel, titanium, and molybdenum alloy.

8. The method of claim 1 wherein the soluble material is a molybdenum chromium alloy and the weld is a nickel, titanium, molybdenum, and chromium alloy.

9. The method of claim 1 wherein the first strut and second strut are part of a single sinusoidal wire.

* * * * *